(12) United States Patent
Smith et al.

(10) Patent No.: US 7,674,433 B2
(45) Date of Patent: Mar. 9, 2010

(54) TUBE FOR STORING FLUID

(75) Inventors: Philip Russel James Smith, Cambridge (GB); Adrian Neil Bargh, London (GB)

(73) Assignee: The Automation Partnership (Cambridge) Limited, Hertfordshire (GB)

(*) Notice: Subject to any disclaimer, the term of this patent is extended or adjusted under 35 U.S.C. 154(b) by 769 days.

(21) Appl. No.: 10/802,871

(22) Filed: Mar. 18, 2004

(65) Prior Publication Data

US 2004/0226984 A1 Nov. 18, 2004

(30) Foreign Application Priority Data

May 13, 2003 (EP) .................................. 03252960

(51) Int. Cl.
*B01L 3/00* (2006.01)
(52) U.S. Cl. ..................................................... 422/102
(58) Field of Classification Search .................. 422/102
See application file for complete search history.

(56) References Cited

U.S. PATENT DOCUMENTS

| 2,240,101 | A | * | 4/1941 | Smith | 422/102 |
|---|---|---|---|---|---|
| 3,759,374 | A | * | 9/1973 | Helger et al. | 206/431 |
| 3,941,300 | A | * | 3/1976 | Troth | 229/5.5 |
| 5,514,343 | A | * | 5/1996 | Verwohlt et al. | 422/104 |
| 6,270,728 | B1 | * | 8/2001 | Wijnschenk et al. | 422/102 |
| D466,219 | S | * | 11/2002 | Wynschenk et al. | D24/227 |
| 6,479,020 | B1 | * | 11/2002 | Stanchfield et al. | 422/102 |
| 2002/0098126 | A1 | * | 7/2002 | Day | 422/102 |

* cited by examiner

*Primary Examiner*—Walter D Griffin
*Assistant Examiner*—Bobby Ramdhanie

(57) ABSTRACT

A tube for storing micro-liter volumes is provided. The tube is open at one end and comprises a body portion of substantially square cross section; a shoulder portion at one end of the body portion and providing the open end of the tube, the cross section of the shoulder portion being greater than that of the body portion; and a formation providing a snap fit connector portion at the other end.

18 Claims, 3 Drawing Sheets

TUBE FOR STORING FLUID

The present invention relates to tubes for containing microliter volumes of fluid and, more particularly, to a tube of low internal volume adapted to engage with a plate.

In many laboratory applications it is preferred to work with increasingly small volumes of fluid. These volumes of fluid are generally stored in small tubes which are, in turn, located in apertures formed in a plate. The plate, with its plurality of tubes, can then be transported from a storage area to a fluid dispensing apparatus. Fluid can be dispensed from the apparatus into the tubes. As a result of the large numbers of these tubes required by modern laboratory practice it is preferable to minimise the size of the plate for a given volume of fluid or number of tubes to be stored.

There are a number of problems associated with the tubes used at present. In general the tubes are circular in cross section and slot into the plate, forming an interference fit between the tube and the plate and slightly deforming the tube. EP-A-0 904 841 discloses a system handling 384-well (aperture) plates in which individual sample tubes are supported in plates in such a way as to be capable of movement into or out of the plates from either side of the plate. To this end the tubes also have a near constant cross-sectional area to enable them to move through the plate.

Some reagents stored within the tubes are volatile or inclined to react with or become contaminated by the surroundings. Therefore it is known to apply a cover to the tube, either in the form of a lamina material that maintains its integrity until pierced or in the form of a self-sealing membrane that allows the tube's contents to remain isolated from the environment even after further reagents have been added to the tube using a dispensing apparatus.

EP-A-0688602 discloses a tube with a collar portion at the base of a shoulder portion. This collar portion provides a means for securing the tube into a plate.

U.S. Pat. No. 6,270,728 discloses a test tube provided with a carrier part disposed on the bottom surface of the test tube onto which a laser can burn an optically recognisable code. The problem with this system is that the size of the optical code is limited by the diameter of the test tube. Therefore as technology moves on and smaller volumes of liquid require smaller tubes to be used this system becomes problematic as the size of the code is limited. U.S. Pat. No. 6,270,728 also discloses a separate collar portion which limits the downward travel of the tube into the rack but provides no resistance to removal.

U.S. Pat. No. 3,554,705 discloses a tube with a rectangular volume at the lower portion through which optical analysis can be made. The optical analysis portion is provided at the lower part of the tube as this is the portion that can be most readily mixed with the magnetic stirring bar.

In some applications there have been problems associated with these closure members, in particular with the closure members maintaining contact with the dispensing tip and therefore causing the tube to be pulled out of its well. This results in the tube being dissociated from its correct position in the plate and, if the dispensing apparatus is not stopped and the array of dispensing tips attempts to dispense to the next row of tubes, the machine may jam, damaging the machine, the tubes and compromising the samples stored in the tubes.

According to the present invention there is provided a tube for storing micro-liter volumes, the tube being open at one end and comprising:

a body portion of substantially square cross section;

a shoulder portion at one end of the body portion and providing the open end of the tube, the cross section of the shoulder portion being greater than that of the body portion; and, a formation providing a snap fit connector portion at the other end.

The tube may further comprise a closure member disposed to close the open end. The closure member may take the form of a foil cap or a self-sealing member, for example a split-septum.

Preferably, the body and shoulder portions are formed separately from the snap fit connector portion.

The snap fit connector portion may have a dot code on it.

The body and shoulder portions may be formed from a translucent or transparent material.

The tube may further comprise a spigot at the interface between the body portion and the snap fit connector portion.

The body portion and the snap fit connector portion may be co-moulded.

The square cross section of the body and the provision of shoulder portions on the tube have a number of advantages. Firstly, the tube fits closely with the aperture in which it is stored without deforming the tube in any way. Secondly, in applications where it is necessary to make an optical reading of the spectrum of the contents of the tube, it is important that the reading is taken through a consistent thickness of the material of the tube and a constant cross section of the fluid. In order to achieve this, when the tube is of circular cross section it is important to line up the optical reading apparatus such that the light beam passes through the diameter of the tube, this maximises the path length through the material contained within the tube and also reduces the effects of refraction from the tube itself. However, using a tube according to the present invention, this precise alignment is unnecessary because the thickness of the material of the tube through which the light passes is the same whatever path across the tube is taken by the light as long as it is perpendicular to one side of the tube.

Furthermore, according to the present invention there is provided A tube for storing fluid, the tube being open at one end and comprising:

a body portion of substantially square cross section;

a shoulder portion at said one end of the body portion and providing the open end of the tube, the cross section of the shoulder portion being greater than that of the body portion; and a flared snap fit connector portion at the closed end of the tube;

said flared snap fit connector portion having an identification code provided thereon.

The flared snap fit connector portion serves two purposes, namely enabling the tube to be snap fitted into a plate and, additionally, providing a surface on which an identification code may be printed. The position of the connector portion at the closed end of the tube allows the identification code to be read while the tube is positioned in a plate.

The flared shape of the connector portion allows a larger code to be used than would be possible if the tube had parallel sides. This flared feature also allows the snap fit action of the connector to fix the tube into the plate.

Preferably the connector and body portions are formed separately from different materials.

The snap fit connector portion is preferably made from a dark plastic which is suitable for laser marking. Laser marking is the preferred form of providing the identification code on the base of the tube, although it would be understood by a man skilled in the art that any other similar process of providing an identification code would be suitable. The body portion is preferably made from a transparent or translucent plastic that allows optical density readings to be made through the body of the tube.

An example of the present invention will now be described with reference to the accompanying drawings in which.

Figure 1:
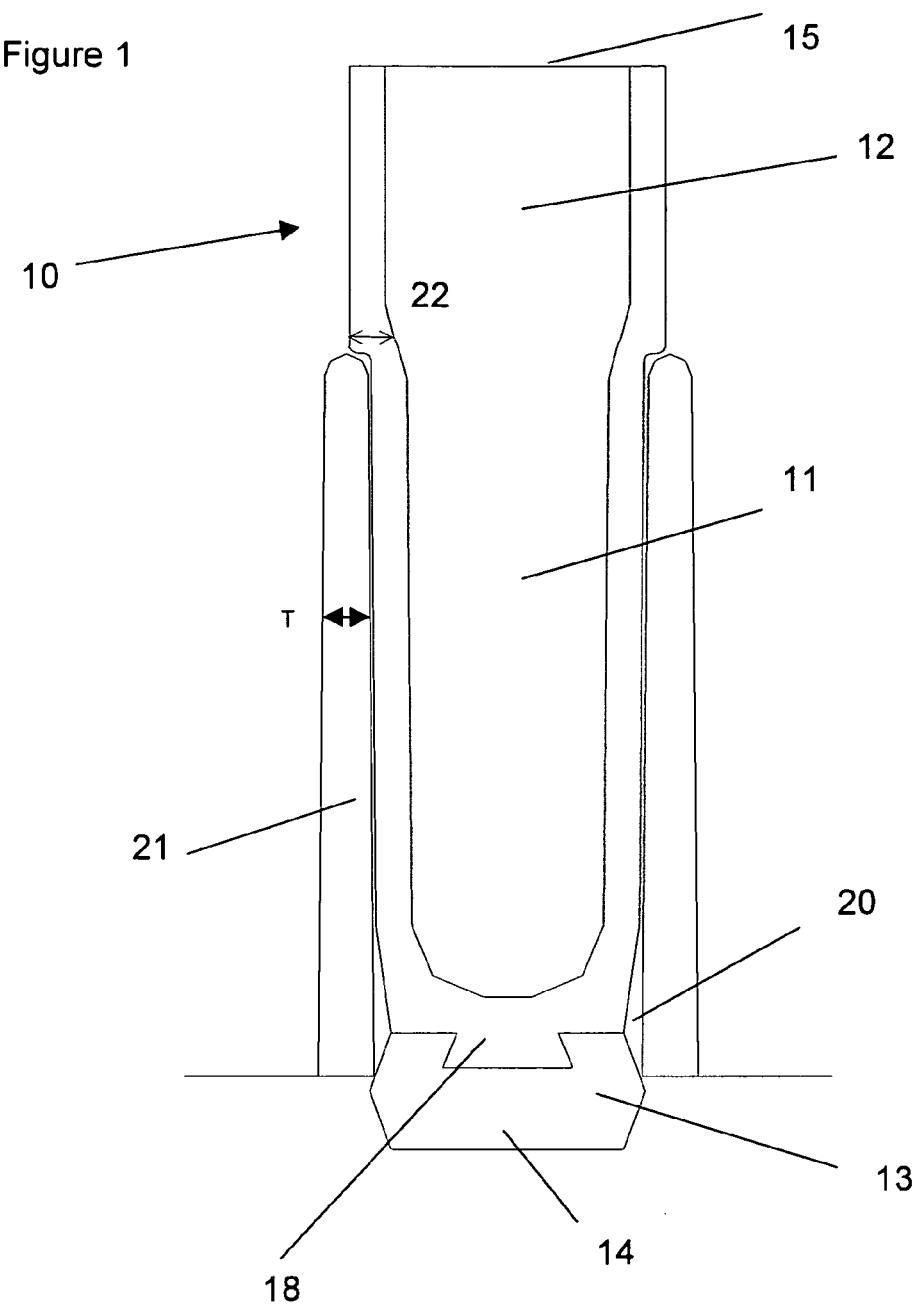
FIG. 1 is a cross section of a tube according to the present invention.

FIG. 1 shows a tube 10 according to the present invention resting in a bore 20 that is formed in a plate containing a plurality of such bores 20. The tube 10 consists of a body portion 11 which has a square cross section. At the top of the body portion 11 of the tube 10, at its open end, is a shoulder portion 12. The shoulder 22 of the shoulder portion 12 allows the tube 10 to engage with the top surface of the bore 20. The shoulder 22 is the same length on all four sides of the tube 10. This prevents the tube 10 from being pushed through the bore 20. In addition the provision of a shoulder portion 12 allows a variety of tubes 10 capable of containing differing volumes to be used in the same size plate. Although all of the bores 20 within a plate are the same size, constraining the volume of fluid that can be held in the body portion 11 the overall volume of the tube 10 can be increased by extending the shoulder portion 12 vertically.

At the bottom of the body portion 11 is a snap fit connector portion 13 that enables the tube 10 to be secured into position within the bore 20 without the bore needing to be adapted in any way. The snap fit connector portion 13 has a profile that tapers outwards from the bottom of the body portion 11 of the tube 10. At the bottom of the connector portion 13 there is a surface 14 onto which a dot code can be printed. This surface 14 is preferably square although it may be round. The snap fit connector portion 13 is preferably constructed from a substance with elastic qualities thereby allowing the connector portion to travel through the bore 20 and then to snap into place at the base of the bore 20 as shown in FIG. 1. The connector portion 13 prevents the tube 10 from being lifted out of the bore 20 unintentionally.

The body and shoulder portions 11, 12 can be formed separately from the snap fit connector portion 13. Alternatively they may be co-moulded. There is a spigot 18 at the bottom of the body portion 11 that interfaces with the snap fit connector portion. The body and shoulder portions 11, 12 are preferably formed from an inert, resilient material, for example polypropylene. The body and shoulder portions 11, 12 are also translucent in order to facilitate the taking of optical spectra of the contents of the tube 10. In contrast, the snap fit connector portion 13 is preferably black in order to maximise the contrast between the laser marked dot code and the connector portion 13. Furthermore, the snap fit connector portion is deformable in order to pass through the bore 20.

The tube 10 is sealed by a sealing member 15 which may be a foil cap or a self-sealing closure member such as a split septum.

Figure 2:
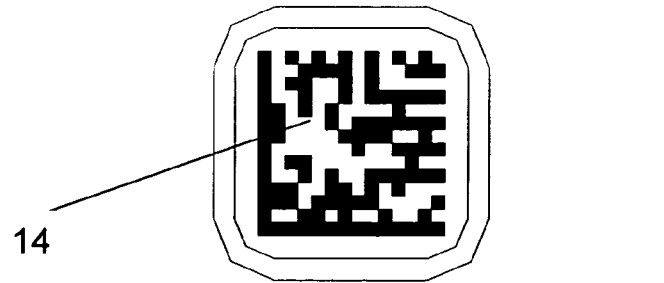
FIG. 2 is a view of the bottom of the tube according to the present invention.

FIG. 2 shows a dot code 16 on the base portion 14 of the snap fit connector portion 13.

Figure 3:
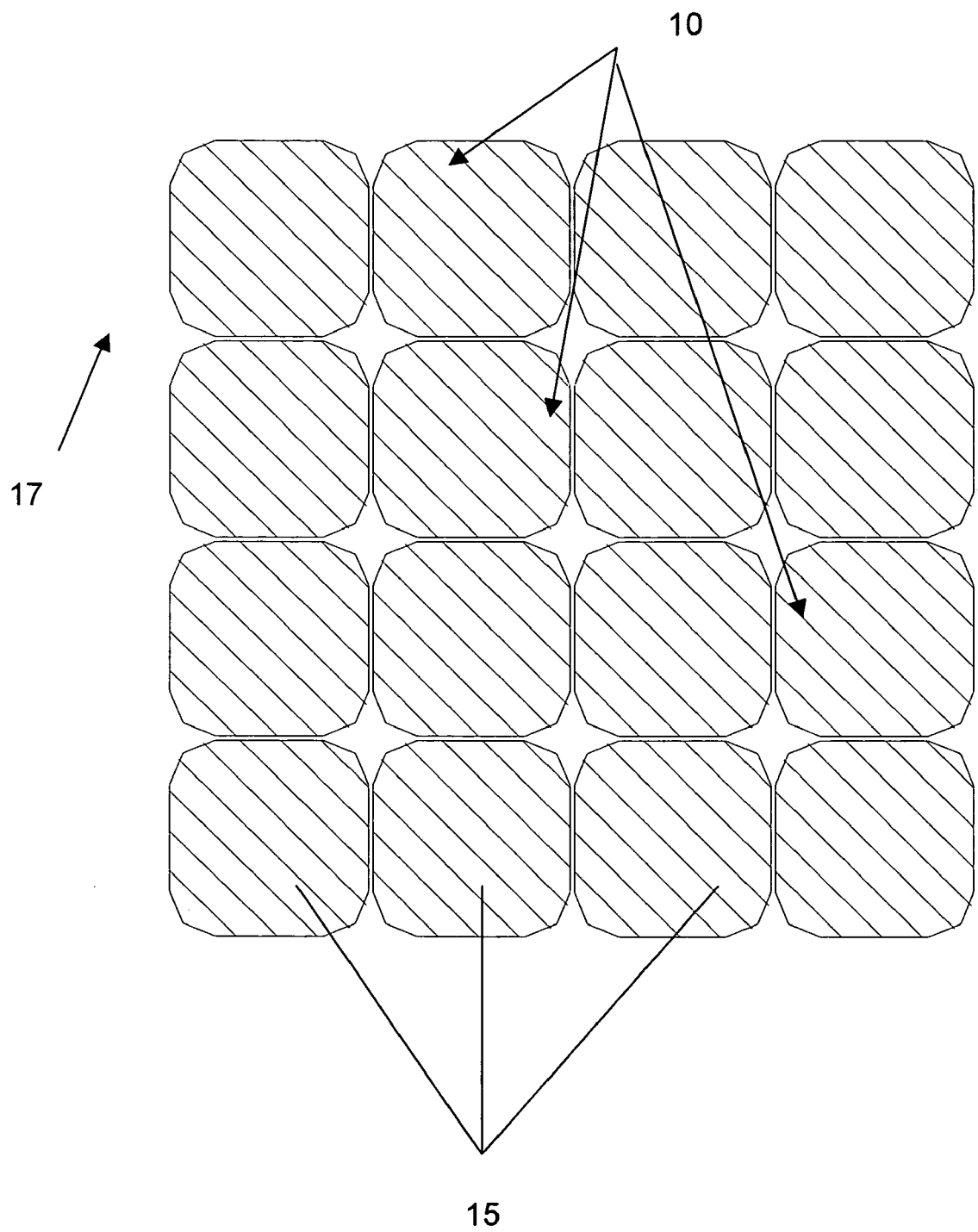
FIG. 3 is a top view of an array of tubes according to the present invention.

FIG. 3 shows a two dimensional array 17 of tubes 10 disposed within a plate 19. The plate 19 forms a grid of bores 20. The plate 19 is constructed from two sets of substantially perpendicular intersecting walls 21. The walls 21 have a thickness T. The length of the shoulder 22 is substantially ½T so that the shoulder portions 12 of the tubes 10 tesselate thereby optimising the use of the space above the plate.

Figure 4:
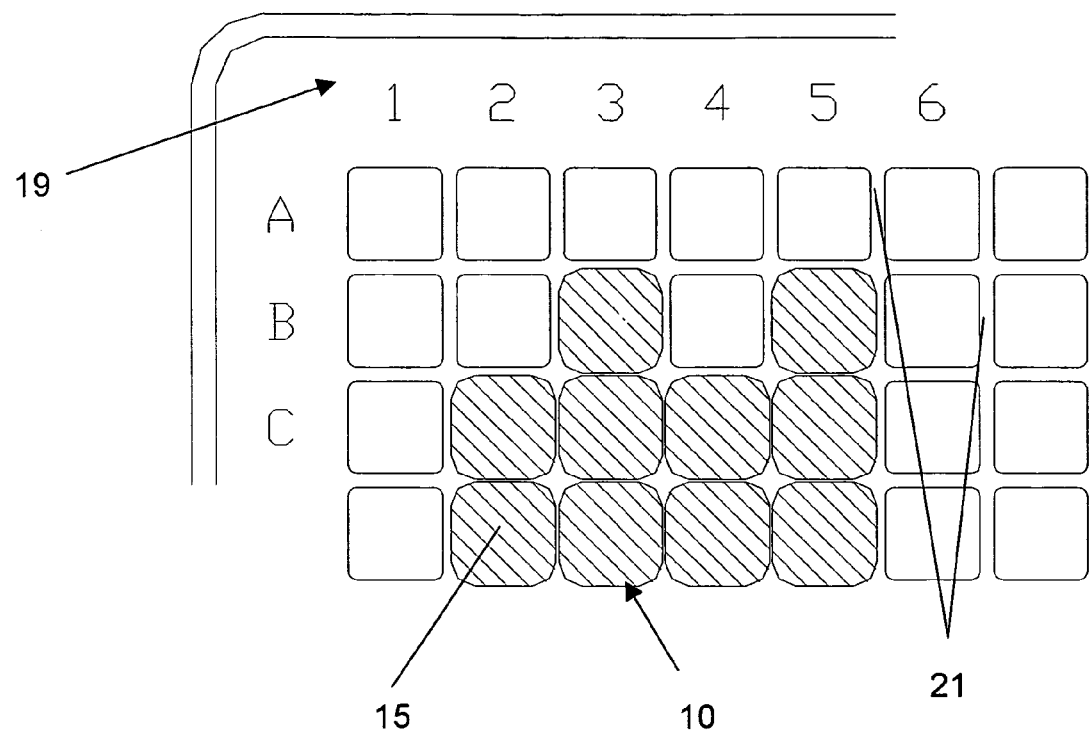
FIG. 4 is a top view of a plate containing a number of tubes according to the present invention.

FIG. 4 shows part of a plate 19 that has been partly-filled with tubes 10.

Figure 5:
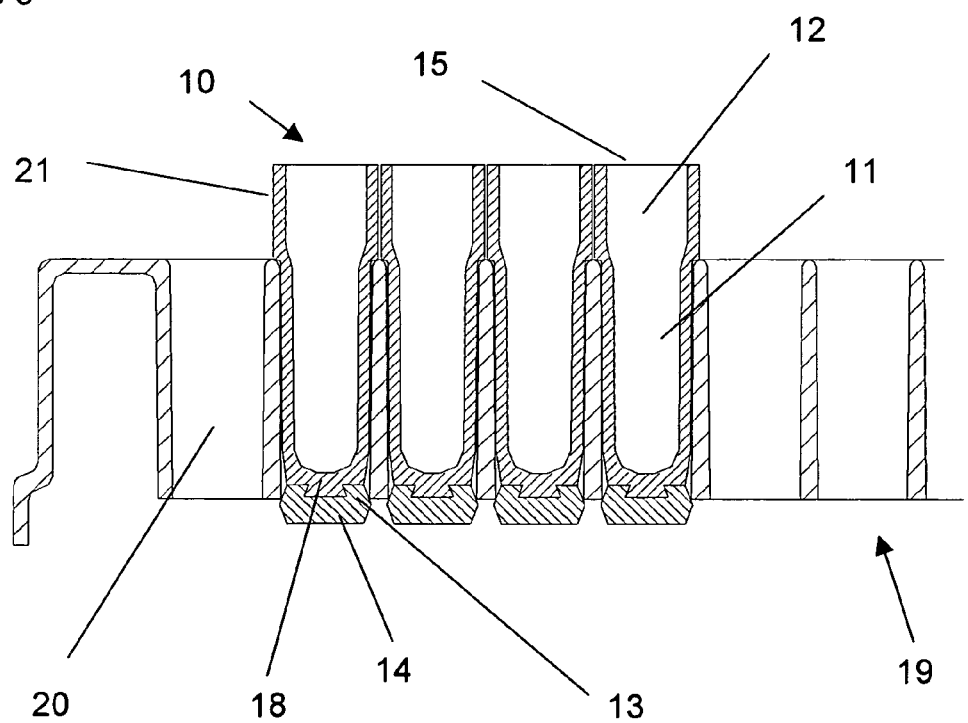
FIG. 5 is a cross section of a plate containing a number of tubes according to the present invention.

FIG. 5 shows a cross section through a plate 19 containing a number of tubes 10. The shoulder portions 12 of the tubes 10 tesselate and thereby use all of the available space above the plate 19.

The invention claimed is:

1. In combination a tube for storing micro-liter volumes and a multi-well plate having a top surface and a bottom surface and through bores having a substantially square cross section parallel to the top and bottom surfaces extending through the plate from the top surface to said bottom surface, said through bores for receiving one tube in a corresponding one of the through bores in said multi-well plate, the tube having first and second ends, the tube being open at the first end and a second closed end, the second end of the tube for engaging the bottom surface of the multi-well plate, the tube comprising:
   a body portion of substantially square cross section corresponding to the cross section of the through bores;
   a shoulder portion near said one end of the body portion and providing the open end of the tube, the cross section of the shoulder portion being greater than that of the body portion; and,
   a deformable formation having a cross section larger than the cross section of the bores providing a connector portion at the second end of the tube, said formation being deformable to fit through the through bore and to extend through the bottom surface to form a snap fit engagement with said bottom surface of the multi-well plate.

2. The combination according to claim 1, further comprising a closure member disposed to close the open end.

3. The combination according to claim 2, wherein the closure member comprises a foil cap.

4. The combination according to claim 2, wherein the closure member is a self-sealing member.

5. The combination according to claim 4, wherein the self-sealing closure member is a split septum.

6. The combination according to claim 1, wherein the body and shoulder portions are formed separately from the snap fit connector portion.

7. The combination according to claim 6, wherein the snap fit connector portion has a dot code on it.

8. The combination according to claim 6, wherein the body and shoulder portions are formed from a translucent or transparent material.

9. The combination according to claim 8, further comprising a spigot at the interface between the body portion and the formation.

10. The combination according to claim 1, wherein the body portion and snap fit connector portion are co-moulded.

11. In combination a tube for storing fluid and a multi-well plate having a top surface and a bottom surface and through bores having a substantially square cross section parallel to the top and bottom surfaces extending through the plate from the top surface to said bottom surface, said through bores for receiving one tube in a corresponding one of the through bores in said multi-well plate, the tube having first open end and a second closed end, the closed end for engaging the bottom surface of the multi-well plate, the tube comprising:
   a body portion of substantially square cross section corresponding to the cross section of the through bores;
   a shoulder portion near said first end of the body portion and providing the open end of the tube, the cross section of the shoulder portion being greater than that of the body portion; and a deformable flared portion at the second end of the tube having a cross section greater than the through bores and being deformable to fit through the through bore and to extend through the bottom surface to form a snap fit engagement with the bottom surface of the multi-well plate said flared portion having an identification code provided thereon.

12. The combination according to claim 11, wherein the connector and body portions are formed separately from different materials.

13. A tube for storing fluid for use with a multi-well plate having a bottom surface and through bores having a substantially square cross section extending through the plate to said bottom surface, said through bores for receiving one tube in a corresponding one of the through bores in said multi-well plate, the tube having a first open end and a second closed end the closed end of the tube for engaging the bottom surface of the multi-well plate, the tube comprising:

a body portion having a substantially square cross section corresponding to the cross section of the through bores;

a shoulder portion near said first end of the body portion above the square cross section, the cross section of the shoulder portion being greater than that of the body portion; and a deformable flared connector portion at the second end of the tube having a cross section greater than the through bores and being deformable to fit through the through bore and to extend through the bottom surface to form a snap fit engagement with the bottom surface of the multi-well plate, said flared connector portion having an identification code provided thereon.

14. A tube for storing fluid comprising:

a body portion having a substantially square cross section, an open upper end and a closed lower end;

a shoulder portion spaced below the upper end, the cross section of the body portion above the shoulder portion being greater than that of the body portion; and a deformable flared connector portion at the lower end of the tube having a cross section greater than the body portion and being deformable, said flared connector portion having an identification code provided thereon.

15. The combination according to claim 1 wherein the shoulder has a cross section larger than the body and the formation has a size larger than the body.

16. The combination according to claim 1 wherein the square cross section of the bore extends between the parallel top and bottom surfaces of the plate and the square cross section of the tube is aligned with the bore.

17. The combination according to claim 1 wherein the snap fit engagement secures the tube in the plate for preventing unintentional separation of the tube from the plate.

18. In combination a tube for storing micro-liter volumes and a multi-well plate having a top surface and a bottom surface and through bores having a substantially square cross section parallel to the top and bottom surfaces extending through the plate from the top surface to said bottom surface, said through bores for receiving one tube in a corresponding one of the through bores in said multi-well plate, the tube having first and second ends, the tube being open at the first end and a second closed end, the second end of the tube for engaging the bottom surface of the multi-well plate, the tube comprising:

a body portion of substantially square cross section corresponding to the cross section of the through bores;

a shoulder portion near said one end of the body portion and providing the open end of the tube, the cross section of the shoulder portion being greater than that of the body portion; and, a deformable formation tapering outwardly from the closed end of the tube having a cross section larger than the cross section of the bores providing a connector portion at the second end of the tube, said formation being deformable to fit through the through bore and to extend through the bottom surface to form a snap fit engagement with said bottom surface of the multi-well plate.

* * * * *